US012478491B2

(12) United States Patent
Hernandez Herasme

(10) Patent No.: US 12,478,491 B2
(45) Date of Patent: Nov. 25, 2025

(54) INSULATING DEVICE FOR AN ULCERATED DIABETIC FOOT

(71) Applicant: Vladimir Florentino Hernandez Herasme, Santo Domingo (DO)

(72) Inventor: Vladimir Florentino Hernandez Herasme, Santo Domingo (DO)

( * ) Notice: Subject to any disclaimer, the term of this patent is extended or adjusted under 35 U.S.C. 154(b) by 327 days.

(21) Appl. No.: 18/014,248

(22) PCT Filed: Dec. 3, 2020

(86) PCT No.: PCT/DO2020/050005
§ 371 (c)(1),
(2) Date: Jan. 3, 2023

(87) PCT Pub. No.: WO2022/012731
PCT Pub. Date: Jan. 20, 2022

(65) Prior Publication Data
US 2023/0233353 A1 Jul. 27, 2023

(30) Foreign Application Priority Data
Jul. 17, 2020 (DO) ................................ P2020-0143

(51) Int. Cl.
*A61F 5/01* (2006.01)

(52) U.S. Cl.
CPC .................................. *A61F 5/0111* (2013.01)

(58) Field of Classification Search
CPC .... A61F 5/0111; A61F 5/0102; A61F 5/0106; A61F 5/0123; A61F 5/0127; A61F 5/0585; A61F 15/008; A61H 2201/164; A61H 2201/1642; A61H 2201/165
USPC .......... 602/23, 26, 27, 14, 16; 128/889, 892, 128/893, 894; 607/88–90, 93, 94
See application file for complete search history.

(56) References Cited

U.S. PATENT DOCUMENTS 3,955,565 A 5/1976 Johnson
5,072,738 A * 12/1991 Wonder ................ A61F 15/008 128/846
5,197,942 A 3/1993 Brady
5,460,599 A * 10/1995 Davis .................... A61F 5/0125 602/26
(Continued)

FOREIGN PATENT DOCUMENTS

CN 201718478 U 1/2011
ES 2611364 5/2017
(Continued)

*Primary Examiner* — Rachael E Bredefeld
*Assistant Examiner* — Seth R. Brown
(74) *Attorney, Agent, or Firm* — David J. Connaughton, Jr.; Justin P. Tinger; Yafei Xue

(57) ABSTRACT

The presently disclosed device is made up of a frame (2) that covers from the distal portion of the thigh of the affected extremity to the soles of the feet and has spacer rings inside (33-36-) of structures made of dry ice (carbon dioxide in a solid state, dry ice), memory foam, among others, atraumatic and non-allergenic when in contact with the user's skin, the frame (2) being divisible into at least two shells, anterior casing (4) and posterior casing (3) that are fixed together by means of a series of hooks for closing the casing (20-24), and the frame (2) having expandable upper and lower support bands (–5.29) of rubber that surround the extremity of the user; covered by a porous mesh (1).

11 Claims, 7 Drawing Sheets

(56) References Cited

U.S. PATENT DOCUMENTS

| | | | | |
|---|---|---|---|---|
| 5,609,570 | A | 3/1997 | Lamont | |
| 6,083,185 | A | 7/2000 | Lamont | |
| 6,726,644 | B1 * | 4/2004 | Pasij | A61F 5/0106 602/26 |
| 2002/0095105 | A1 | 7/2002 | Jensen | |
| 2002/0138030 | A1 | 9/2002 | Cavanagh et al. | |
| 2010/0010408 | A1 * | 1/2010 | Linares | A61F 13/046 602/14 |
| 2010/0204631 | A1 | 8/2010 | Rooney | |
| 2012/0116275 | A1 * | 5/2012 | Pochatko | A61F 5/0111 602/27 |
| 2013/0116612 | A1 * | 5/2013 | Stephan | A61N 5/0616 604/319 |
| 2018/0125693 | A1 * | 5/2018 | Best | A61F 5/0109 |
| 2020/0038216 | A1 * | 2/2020 | Hanna | A61F 5/0123 |

FOREIGN PATENT DOCUMENTS

| | | | | |
|---|---|---|---|---|
| GB | 2318059 | A * | 4/1998 | A61F 15/008 |
| JP | 2009518554 | | 5/2009 | |
| MX | 2017002122 | | 5/2019 | |
| MX | 2019008461 | | 9/2019 | |

* cited by examiner

INSULATING DEVICE FOR AN ULCERATED DIABETIC FOOT

TECHNICAL FIELD

The present invention relates to the field of medical devices used in diabetology, wound care, and dermatology. It is an external device that facilitates the treatment and healing of diabetic foot wounds by isolating the leg and allowing prolonged exposure of the ulcer and/or wound to environmental factors such as oxygen and other important elements of the environment, including ultraviolet rays, temperature, and humidity. This exposure helps keep the wounds dry and free of pathogenic microorganisms, thereby contributing to rapid tissue regeneration.

DESCRIPTION OF THE PRIOR ART

Diabetic Foot is a complication arising from impaired circulation in the small blood vessels of diabetic patients with chronic uncontrolled blood glucose levels. This condition leads to vascular obstructions that cause ulcerations, typically triggered by trauma, pressure, or friction during activities such as walking or standing, compounded by a loss of sensation. These ulcers are difficult to heal, and infections often become deep and severe due to the patients' reduced immune defense. As a result, local microorganisms proliferate, and pathogens from the environment can easily contaminate the wounds, which remain exposed both directly and indirectly.

Currently, 8.5% of the global population suffers from diabetes, with the prevalence of Diabetic Foot pathology ranging from 1.3% to 4.8%. However, other estimates—taking into account factors such as sex, age, and population type—suggest a prevalence between 4% and 10%. The most common contributing factors are of neural origin, accounting for 45% to 60% of cases, while purely ischemic causes represent 10% to 15%. Alarmingly, this condition leads to a leg amputation somewhere in the world every 30 seconds.

Treatment for patients with ulcers typically involves cleaning the wounds thoroughly, including proper debridement, followed by covering them with gauze and antibiotic cream or spray, or gauze alone, depending on the presence of infection. This approach helps protect the wound from external contaminants, prevents infection, and promotes the growth of new tissue.

Covering wounds with gauze helps prevent contact with external agents such as flying insects, saliva droplets (Flügge droplets), environmental dust, and other contaminants. However, this practice can create a local environment that hinders effective healing due to retained moisture and reduced oxygen supply. The accumulation of serum and wound debris beneath the covering impairs epithelialization and promotes the formation of a bacterial broth, which deepens the ulcer.

Using a cold air blower (such as a hair dryer on a cool setting) directly on the wound helps keep it dry, thereby promoting more effective closure. This drying method is central to the treatment with the APDU device, although the insulation device itself can function without it-albeit requiring longer healing times. Combined with topical and/or oral antibiotics, healing creams, vitamins, and bee-derived propolis drops, this approach facilitates significant wound improvement within one week of applying the insulation and drying treatment, with exposure to environmental factors.

Based on these observations and the limitations of conventional treatments recommended by Diabetic Foot guidelines, a device was developed to create an optimal environment that maintains wound dryness while isolating it from environmental contaminants, thereby reducing infection risks.

Existing inventions aimed at preventing diabetic foot complications are mostly prophylactic, such as protective boots designed to reduce pressure and prevent rough contact with the ground, thereby minimizing skin damage and infection risk in vulnerable patients. Devices intended for treating existing ulcers primarily focus on offloading pressure and providing comfort rather than controlling wound moisture or isolation.

A survey of approximately twenty external-use medical devices for diabetic patients revealed the following categories: three insoles, one diagnostic device, three splints, two anti-shock boots, and two bandages for topical medication. Their mechanisms primarily address pressure reduction, wound prevention, pus drainage, and topical medication delivery, rather than humidity control.

Some notable inventions include:

Insole for Treatment and Prevention of Ulcers (ES2611364A1): Cushions weight and adapts to foot shape through special porosity.

Insole for Protection of Diabetic Foot (MX2017002122A): Redirects load to reduce pressure and friction, incorporates antibiotic nanoparticles.

Apparatus for Diagnosis of Diabetic Foot (2019008461A): Predicts diabetic foot development using vibration waves emitted by a motor.

Personalized Foot Orthosis (U.S. Pat. No. 5,197,942A): Allows atraumatic mobility while admitting airflow through an open space to improve healing.

Orthopedic Protection and Splint Medical Boot (U.S. Pat. No. 5,609,570A) & Medical Foot Device (U.S. Pat. No. 6,083,185A): Orthopedic shoes that cushion the foot, with the latter including a fluid cushion to reduce pressure.

Methods and Apparatus for Treatment of Plantar Ulcers (US20020095105A1): Minimizes body weight on the ulcer and restricts foot curvature to aid healing.

Wound Healing System and Method (US20020138030A1): Enables load relief on the plantar foot and automatic drainage in ulcerated areas.

Device for Treatment of Plantar Ulcers and Foot Deformities (US20100204631A1): Treats ulcers and corrects foot deformities through orthosis.

Pharmaceutical Composition and Device for Ulcer Prevention and Healing (US2029/0310): Includes medicinal compounds such as snail slime (Cryptophalus *aspersus* or *Helix aspersa* muller species) with pharmaceutical carriers.

Socks for Diabetics (CN201718478U, JP2009518554A): Designed to relieve pressure and protect bony prominences, some apply positive ions to the feet.

TCC-EZ Diabetic Foot Ulcer Treatment Splint System (U.S. Pat. No. 3,955,565A): Orthopedic device providing lower limb protection.

These inventions largely focus on prevention, pressure offloading, or medication delivery, and do not directly address the control of moisture or isolation of ulcers from environmental pathogens—a gap the present device aims to fill.

DESCRIPTION OF THE INVENTION

The Insulating Device for an Ulcerated Diabetic Foot (APDU) is designed to promote the healing of ulcers associated with Diabetic Foot disease by creating an optimal environment for wound repair. This is achieved through an indirect mechanism that accelerates wound resolution by increasing exposure to daylight and prolonged oxygen contact, while simultaneously preventing the invasion of biological agents such as flies, mosquitoes, fungi, bacteria, viruses present in saliva droplets, and inert contaminants like dust, all of which can interfere with the healing process.

The device has an ergonomic and visually appealing design intended to ensure patient acceptance and provide comfortable rest, which is essential for recovery. The APDU comprises a posterior casing and an anterior casing that cover the affected limb from the distal portion of the thigh to the soles of the feet. These casings incorporate support areas that contact the user's skin and are divisible into at least two parts connected by hooks located on the internal and external sides of the frame.

At the distal thigh, above the knee, the device includes a continuous wide ring made of rubberized material with vertical hollow female-type structures, which have closed upper ends and open lower ends to receive vertical bars. Other support rings, except for the one at the ankle, consist of four quarter-moon shaped segments arranged on the inner surface of the casing in the internal, external, anterior, and posterior positions. The side segments are divided between the anterior and posterior casings. The thickness of these segments can be adjusted to meet safety and functional requirements. The ankle support is a complete rubberized ring similar to the upper ring but equipped with rigid hinge-like 35 structures joined by pins, allowing attachment of bars via these hinges rather than insertion into hollow structures.

The materials used in the support areas are atraumatic and hypoallergenic, such as materials similar to dry ice or memory foam, to ensure comfortable contact with the skin. At the rear of the casing, between the upper and lower leg, there is a Rest Support Base Assembly designed to support the leg when the user is seated or lying down. This assembly consists of two parallel round bars with slots that accommodate a thin, rigid sheet forming the base. Rigid adhesion supports connect this structure to the posterior casing, creating a stable resting surface. Pads providing comfort are positioned over the gastrocnemius muscle and the ankle area; these pads are removable as needed.

The device features six vertical bars arranged in frontal, posterior, and lateral (internal and external) positions running longitudinally along the leg. The front and rear bars extend down to the plantar base, where they curve forward or backward near the heel to join the lateral bars, thus forming the casing. The heel area is supported by a ring and lateral bars, while the plantar base consists of multiple crossbars arranged to create a stable foot enclosure.

To maintain a dry wound environment essential for healing, the device incorporates a fan that may be a purpose-designed unit or a hair dryer operating in cold mode. This fan is secured to the casing with a fastening strap and positioned between the plantar area and the back of the foot using a closing clasp. Additionally, a fluorescent ultraviolet lamp is integrated into the device to inhibit microbial growth and provide prophylactic action against opportunistic pathogens. Both the fan and lamp are controlled by a single on/off switch, with the lamp featuring an automatic intermittent activation timer. The device can be powered by an AC power source with a long supply cord or by batteries to provide the patient with mobility.

In clinical use, the device is combined with topical or oral antibiotics, healing creams, vitamins, and propolis drops to facilitate effective tissue proliferation and significant wound improvement within weeks of treatment.

DETAILED DESCRIPTION OF THE INVENTION

Figure 1:
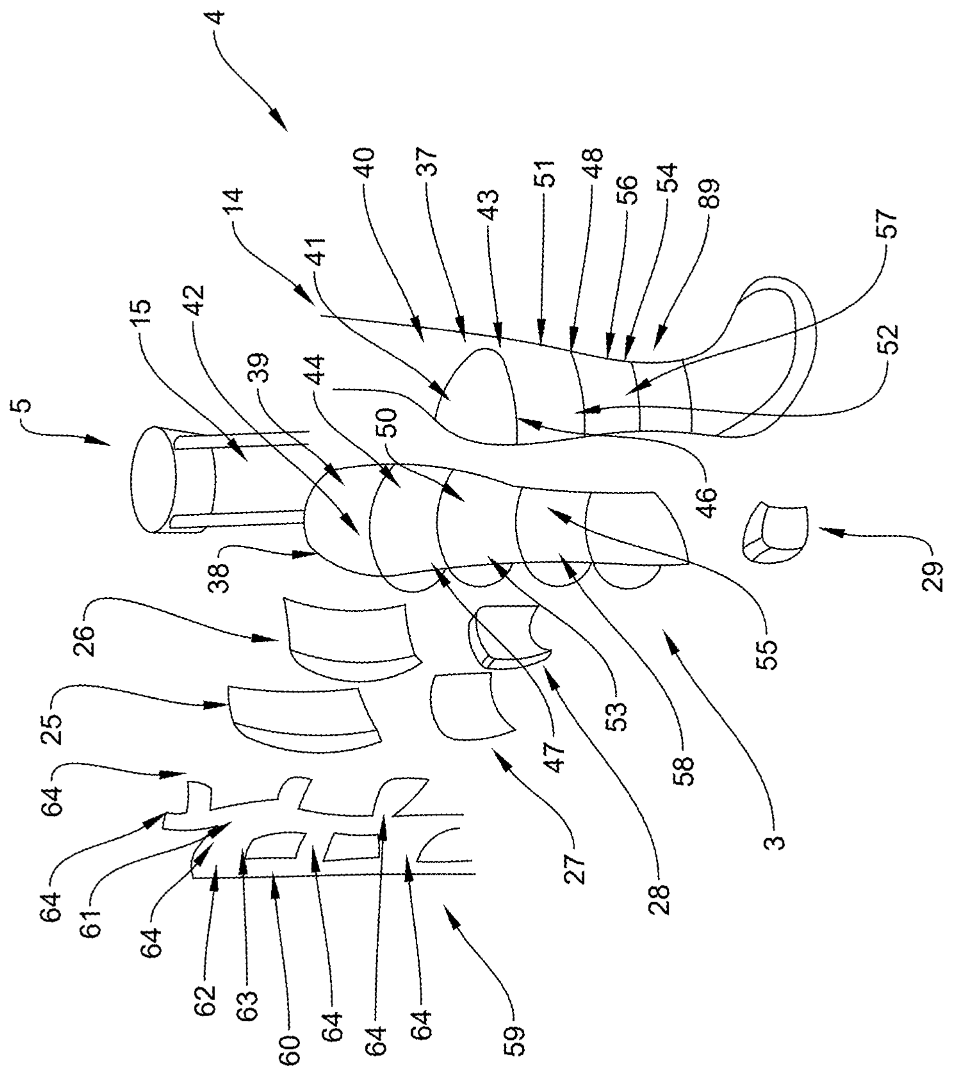
FIG. 1 shows an exploded view of the Insulating Device for an Ulcerated Diabetic Foot (APDU) with its individual components.
Figure 2:
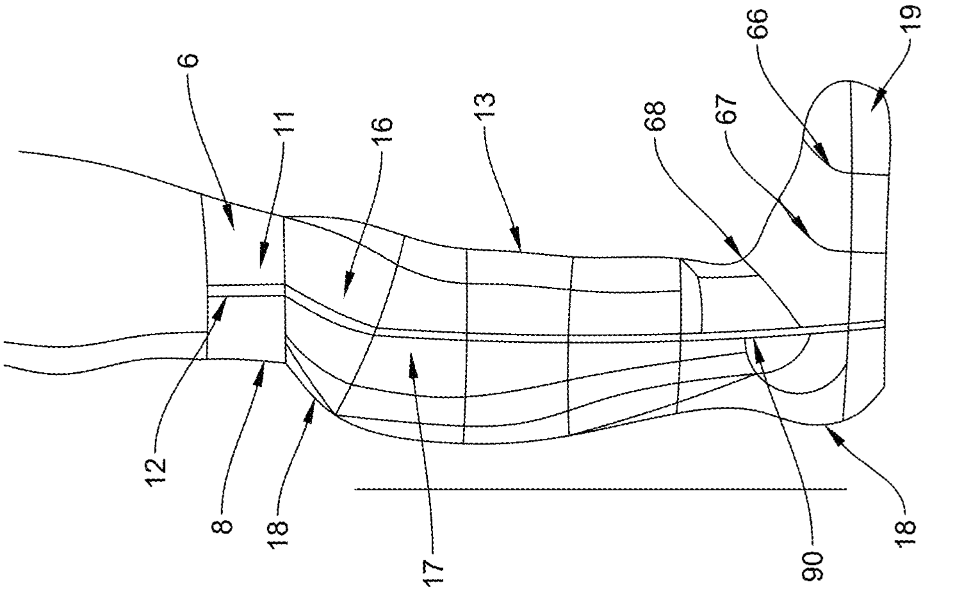
FIG. 2 presents a right side view of the APDU without the insulating mesh.
Figure 3:
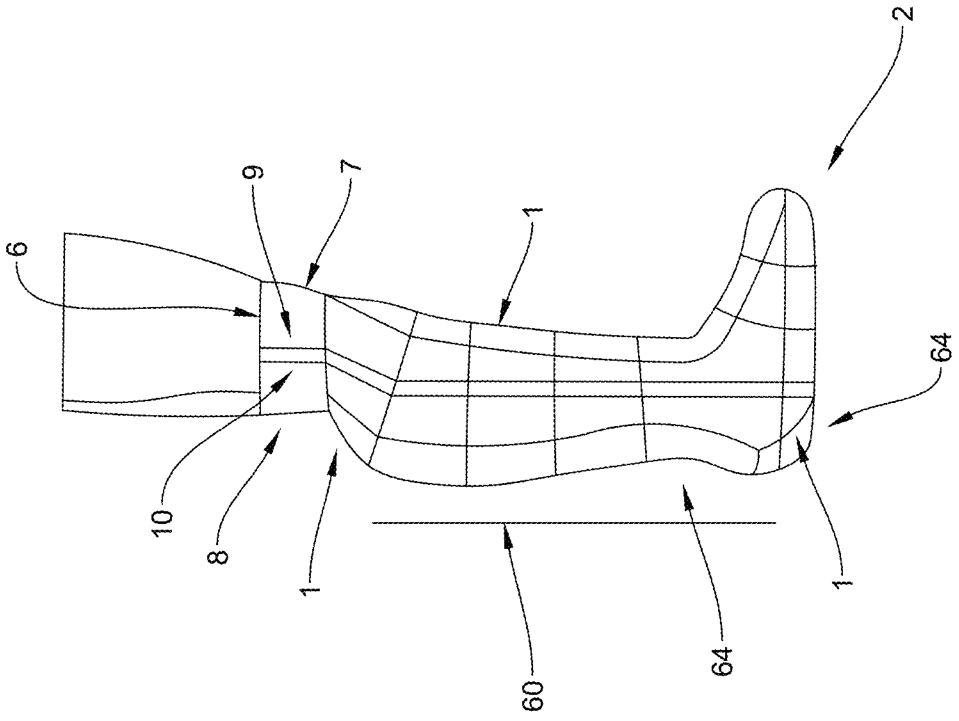
FIG. 3 depicts a right side view of the APDU with the insulating mesh installed, illustrating some of its components.
Figure 4:
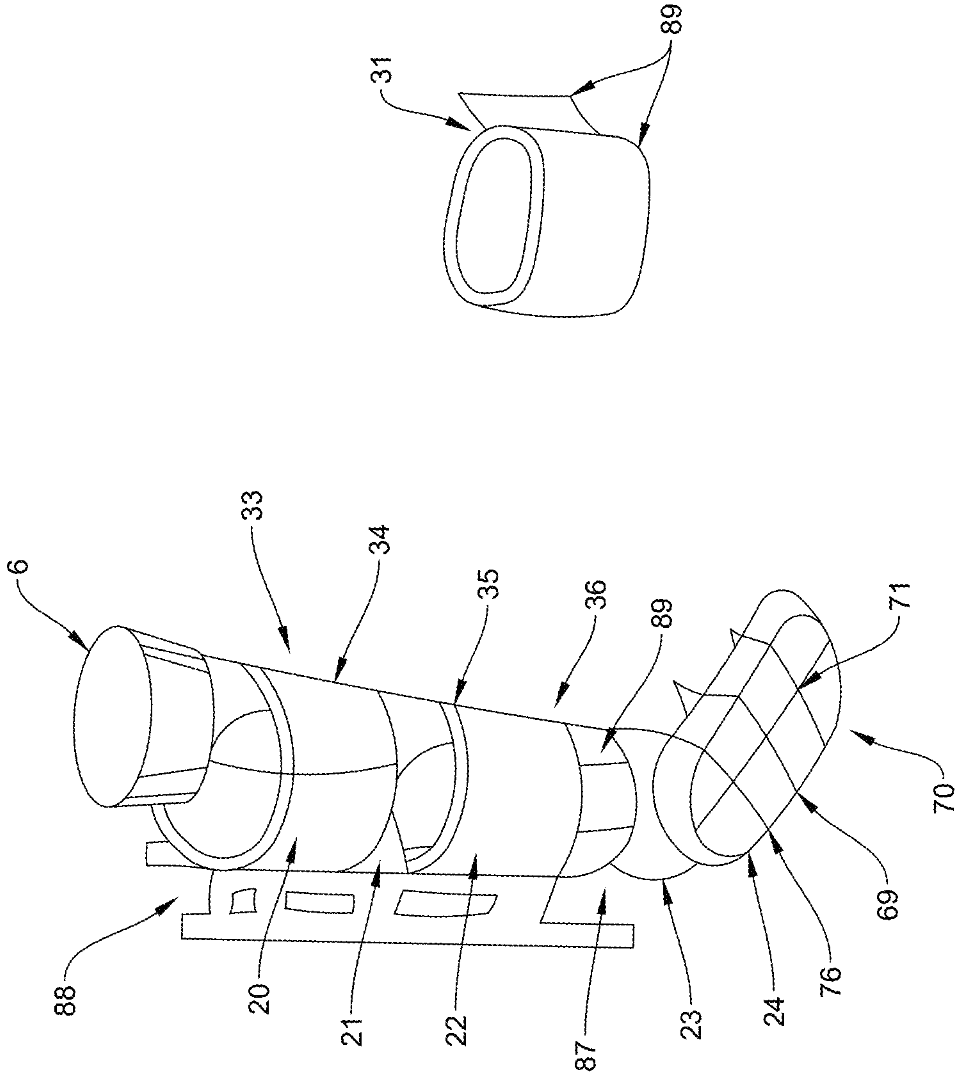
FIG. 4 provides a right isometric view of the APDU, excluding the user and partially showing its components.
Figure 5:
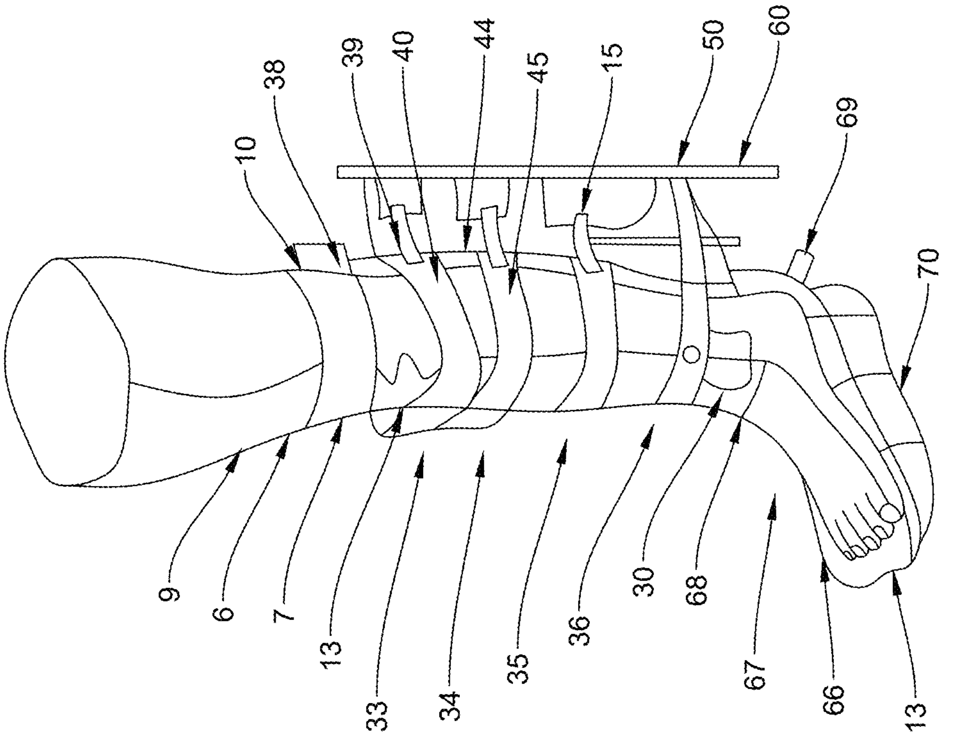
FIG. 5 shows a left isometric view of the APDU without the mesh, including the user and displaying its parts and components.
Figure 6:
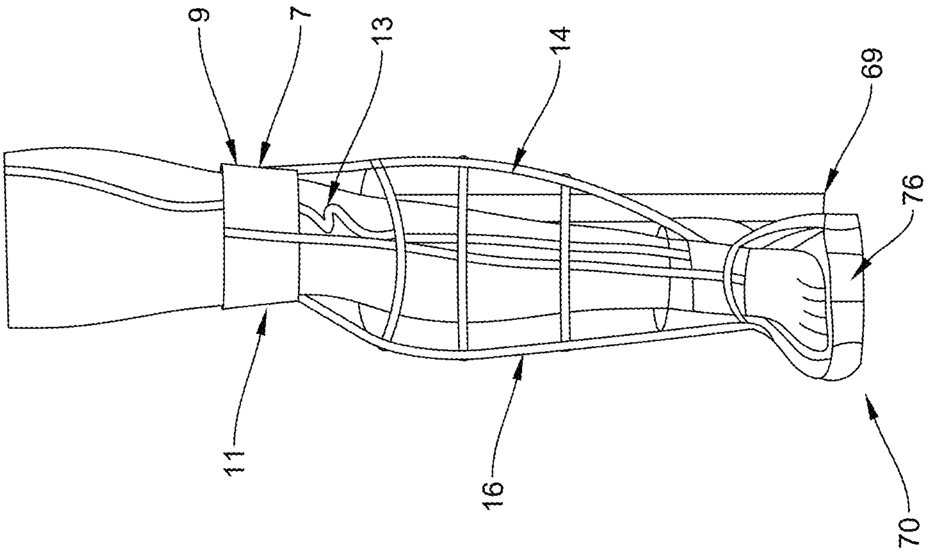
FIG. 6 is a front view of the Insulating Device for an Ulcerated Diabetic Foot.
Figure 7:
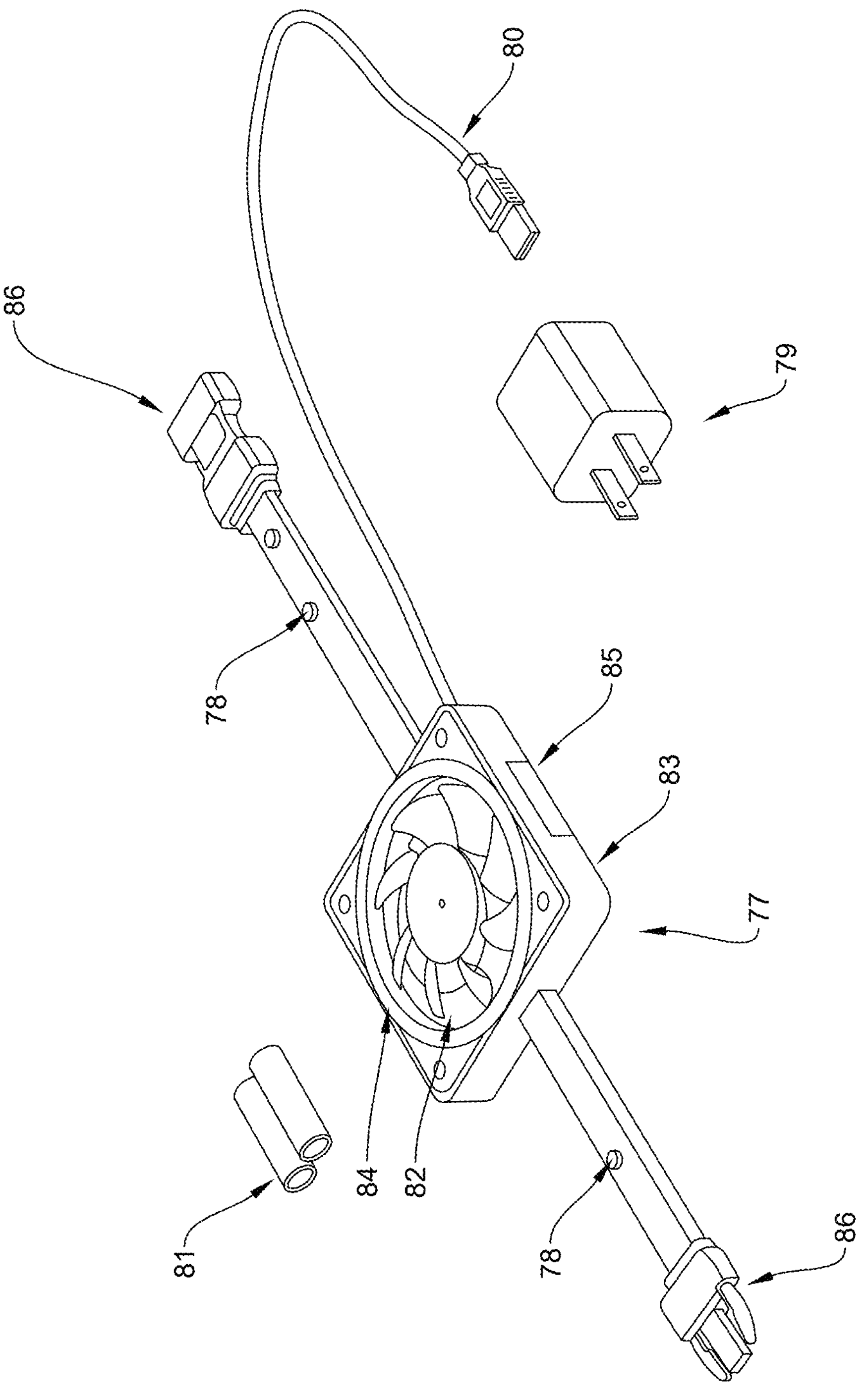
FIG. 7 illustrates a front view of the fan, fluorescent lamp, and associated parts and components, including batteries, cable, and power supply.

The Insulating Device for an Ulcerated Diabetic Foot (APDU) is a medical device designed to be worn on the leg as a frame (2) composed of a rear casing (3) and a front casing (4), covering the affected limb from the distal portion of the thigh (above the knee) down to the soles of the feet. The rear casing (3) and front casing (4) fit snugly to the leg and foot, enclosing these anatomical areas and isolating them from the environment by means of a mesh (1), which may be made of mosquito netting or a highly porous fabric similar to women's pantyhose. This mesh rests on and extends over the casing, creating a barrier that prevents external pathogens from entering.

The device is secured to the leg through specific contact points that serve as supports (5, 24), providing stability and immobilization, combined with spacers (39-60) made of semi-rigid, comfortable, and hypoallergenic materials such as viscoelastic foam (memory foam) or solid carbon dioxide (dry ice). The casing or frame (2) of the APDU is designed to be easily disassembled, facilitating sanitation of the leg and foot by removing the disposable mesh (1), which can be replaced in the reusable version or attached in the disposable version. Complete exposure of the limb is achieved by separating the rear casing (3) from the front casing (4) after first disengaging the closing hooks (20-24) located on both sides of the device.

From a cephalo-caudal perspective, the device includes an upper support band (5) featuring six female adapters (7-12) made from pressure-resistant material, spaced equidistantly as follows: front adapter (7), rear adapter (8), two internal side adapters (9, 10), and two external side adapters (11, 12). These adapters have closed upper ends and open lower ends designed to receive vertical bars, which are named according to their anatomical axis and position.

Six vertical bars are arranged depending on the version, made either from plastic or other rigid yet lightweight materials such as aluminum. The device offers both disposable and reusable versions depending on the materials used. The bars include an anterior vertical bar (13); four lateral vertical bars consisting of the anterior internal vertical bar (14), posterior internal vertical bar (15), anterior external vertical bar (16), and posterior external vertical bar (17); and a descending posterior vertical bar (18). The anterior vertical bar (13) and descending posterior vertical bar (18) extend downward from the upper ring (5) toward the foot. At the plantar base (19), they curve, with the posterior descending bar (18) bending forward and the anterior bar (13) bending backward, forming a false joint at the heel area. These bars complement the lateral bars to form the anterior (4) and rear (3) casings.

Continuing downward, a series of spacers form discontinuous rings (33-36) between the upper support (5) and the lower support (29). The rear casing spacers connect to the posterior external vertical bar (17), posterior internal vertical bar (15), and descending posterior vertical bar (18), while the front casing spacers connect to the anterior external vertical bar (16), anterior internal vertical bar (14), and anterior vertical bar (13). Four discontinuous spacer rings are located in this space: ring A (33) below the knee, ring B (34) at the gastrocnemius muscles (notably lacking posterior support due to the leg resting on a large pad (26)), ring C (35) between the gastrocnemius and ankle areas, and ring D (36) at the ankle, also without a posterior spacer. Spacers are labeled according to their ring and position, using initials such as DEL for front, POS for rear, LATiDEL and LATiPOS for front and rear internal sides, and LATeDEL and LATePOS for front and rear external sides, combined with the ring letter (e.g., BLATiDEL (45)).

Ring A (33), below the knee in the upper third of the leg, consists of four quarter moons serving as spacers (37-42). Side spacers are divided into front (40, 41) and rear (39, 42), each attached internally to the casing. This description is representative of all spacer rings, even if certain rings lack posterior spacers at specific levels.

The foot portion of the frame comprises five nearly circular rings (66-70), three oriented with their openings perpendicular to the front face of the heel area (front, middle, and rear rings: 66, 67, 68), and two oriented transversely with openings parallel to the plantar base face (upper and lower plantar rings: 69, 70). The heel zone is bounded superiorly by the posterior hoop (68), laterally by the posterior external vertical bar (17) and posterior internal vertical bar (15), and inferiorly by three plantar crossbars (anterior, middle, and posterior), intersected perpendicularly by a lower plantar sagittal bar (71), together forming the plantar base (19). An optional insole space (76) of approximately half to one inch is provided between the plantar surface and the inner face of the APDU to accommodate an insole if desired.

The front and rear casings are secured by several closing hooks (20-24), located on the external and internal vertical bars (14-17) at specific points including ring B (34), ring C (35), near the ankle area (87), and at the plantar base adjacent to the lower plantar ring (70).

The APDU integrates a fan (77) designed to direct airflow onto the wound to maintain dryness. The fan is attached via a retaining strap (78) that secures it firmly to the casing. It can be powered by an AC power supply (79) or by batteries (80) for DC power. The power cable (81) exceeds five meters in length, allowing user mobility. The fan's blades (82) generate the airflow and the fan includes a fluorescent lamp (84) emitting ultraviolet light, equipped with an automatic timer to control intermittent operation. The ultraviolet light serves to inhibit microbial growth and aids in wound treatment and prophylaxis. The fan and lamp positions are adjustable using the retaining strap (78) and secured with a resistant closing clasp (86), which requires lateral pressure to engage. Control switches on the fan's sides operate the fan (83) and ultraviolet light (85) independently.

For patient comfort, the APDU features a rest support base assembly (CBAD) (59) enabling the leg to rest when seated or lying down. The CBAD includes two long support bars (60) with parallel slots forming a 90-degree angle in cross-section. One slot receives a rectangular flat base (62), joining the two bars via this base (63). The other slot accommodates three pairs of adhesion supports (64) that attach to the rear casing (3), completing the support base assembly (59).

The rear casing (3) incorporates four key structures: a large pad tray (25), a large pad (26), a small pad tray (27), and a small pad (28). The large pad tray (25), located at the gastrocnemius muscle level, is concave internally and slightly convex externally. The large pad (26) rests on the tray, providing support for the leg during rest and is held in place by adhesive. Similarly, the ankle region includes a small pad tray (27) and small pad (28) offering comparable support.

The invention claimed is:

1. An isolator of an ulcerated diabetic foot, comprising:

a frame being divisible into an anterior shell and a posterior shell, wherein the posterior shell comprises a set of support bases;

wherein the anterior shell and posterior shell are fixed to each other by a series of shell closing hooks;

wherein the anterior shell and posterior shell comprise spacer rings, the spacer rings are made of an atraumatic material and are non-allergenic;

wherein at least one of the spacer rings comprises four quarter moon shaped protrusions on an internal surface of the frame;

wherein the frame comprises an upper support and a lower support, the upper support and the lower support are both made of an elastic band, the upper support is configured to surround a limb of a user above a knee and the lower support is configured to surround the limb of the user at the level of an ankle to give firmness to the frame;

wherein the anterior shell and the posterior shell include a relocatable fan comprising a fluorescent lamp that emits ultraviolet light; and a porous mesh that is placed around the frame.

2. The isolator of an ulcerated diabetic foot according to claim 1, characterized in that the frame has an anterior vertical bar, a posterior internal vertical bar, an anterior internal vertical bar, an anterior external vertical bar, a posterior external vertical bar and a posterior vertical bar, and the spacer rings comprise four spacer rings.

3. The isolator of an ulcerated diabetic foot according to claim 1, characterized in that the set of support bases are in the shape of a rectangle formed by two support bars having a slot on a length of the support bars, and where the two support bars are placed one on each side of the frame and joined by a flat rectangular base.

4. The isolator of an ulcerated diabetic foot according to claim 1, characterized in that the fan incorporates a fan fastening strap that is firmly fixed to the frame and the fluorescent lamp emits its rays in the direction the fan faces, and wherein the fan is powered by a battery or an AC power supply connected to the fan.

5. The isolator of an ulcerated diabetic foot according to claim 4, characterized in that the fan is made up of tiny blades that are configured to blow air towards a wound of the user.

6. The isolator of an ulcerated diabetic foot according to claim 1, characterized in that the porous mesh is made of a mosquito net or highly porous female stocking, with tiny holes that rest and extend on the outside of the frame.

7. The isolator of an ulcerated diabetic foot according to claim 4, characterized in that the fluorescent lamp is adjusted in front of the fan such that the fluorescent lamp emits ultraviolet rays in the direction of a wound of the user.

8. The isolator of an ulcerated diabetic foot according to claim 1, characterized in that fixed to an internal face of the posterior shell is a large tray for a large pad, wherein the large pad is configured to be placed at the level of the ankle of the user; and a small tray for a small pad;

wherein both the large tray and the small tray are fixed to a posterior bar.

9. The isolator of an ulcerated diabetic foot according to claim 8, characterized in that the large pad and the small pad each have a front side lined with a non-allergenic fabric and a back side smeared with adhesive that allows the large pad to be kept fixed to the large tray and the small pad to be kept fixed to the small tray while being removable.

10. The isolator of an ulcerated diabetic foot according to claim 1, characterized in that the lower support has rubberized hinges fixed to the elastic band and to the frame, and wherein both parts of the hinges are joined by a pin.

11. The isolator of an ulcerated diabetic foot according to claim 1, characterized in that the frame further comprises a foot frame;

the foot frame is made up of an anterior ring, a middle ring and a posterior ring each positioned such that a hole of the anterior ring, the middle ring and the posterior ring are parallel to a hole on a front face of the foot frame;

the foot frame is further made up of an upper plantar ring and a lower plantar ring that are oriented such that a hole of the upper plantar ring and the lower plantar ring point parallel to a face of a plantar base, which is transverse to the anterior ring, the middle ring and the posterior ring;

a heel zone is delimited in a lower portion of the frame superiorly by the lower support, laterally by both a posterior external vertical bar and a posterior internal vertical bar; and three plantar crossbars.

* * * * *